United States Patent [19]
Cragoe, Jr. et al.

[11] 3,958,004
[45] May 18, 1976

[54] PHENOXYACETIC ACID DERIVATIVES AS URICOSURIC AGENTS

[75] Inventors: Edward J. Cragoe, Jr., Lansdale; George M. Fanelli, Jr., Penllyn, both of Pa.

[73] Assignee: Merck & Co., Inc., Rahway, N.J.

[22] Filed: Apr. 23, 1974

[21] Appl. No.: 463,227

[52] U.S. Cl............................. 424/275; 424/250; 424/285
[51] Int. Cl.² ............... A61K 31/38; A61K 31/495; A61K 31/34
[58] Field of Search.................... 424/275, 285, 250

[56] References Cited
UNITED STATES PATENTS
3,758,506   9/1973   Godfroid et al. ................... 424/275

*Primary Examiner*—Donald B. Moyer
*Attorney, Agent, or Firm*—Michael C. Sudol, Jr.; J. Jerome Behan; Rudolph J. Anderson

[57] ABSTRACT

[2,3-Dichloro-4-(2-thenoyl)phenoxy]acetic acid, [2,3-dichloro-4-(5-methyl-2-thenoyl)phenoxy]acetic acid and [2,3-dichloro-4-(2-furoyl)phenoxy]acetic acid and their pharmaceutically acceptable salts are uricosuric agents useful in the treatment of hyperuricemia.

4 Claims, No Drawings

PHENOXYACETIC ACID DERIVATIVES AS URICOSURIC AGENTS

BACKGROUND OF THE INVENTION

The compounds used in this invention and methods for their preparation are known in the art and are shown in U.S. Pat. No. 3,758,506, patented Sept. 11, 1973 to Jean Jacques Godfrold and Jean Eugene Thuillier assigned to C.E.R.P.H.A. In this patent, the above compounds, particularly the [2,3-dichloro-4-(2-thenoyl)phenoxy]-acetic acid or its pharmaceutically acceptable salts thereof are shown to be strong diuretic agents.

SUMMARY OF THE INVENTION

This invention relates to a new use for compounds of the formula:

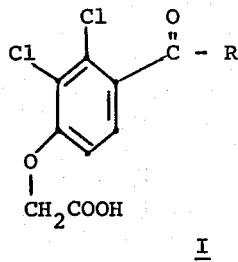

I wherein R can be 2-thienyl, 5-methyl-2-thienyl or 2furyl and the pharmaceutically acceptable salts thereof.

Applicants have found that the compounds of Formula I in addition to being effective diuretic and saluretic agents are uricosuric agents in that they cause a sharp increase in uric acid excretion and a secondary decrease in plasma uric acid concentration. Thus, the compounds of Formula I are able to maintain the uric acid concentration in a human body at pretreatment levels or to even effect a decrease in the uric acid concentration. Furthermore, the invention relates to pharmaceutical compositions for this use containing the compounds of Formula I.

When administered in therapeutic dosages, in conventional vehicles, the compounds of Formula I effectively increase the excretion of sodium and chloride ions in the urine and, in general, alleviate conditions usually associated with edema. In addition, these compounds overcome a major problem associated with many of the presently available diuretic-saluretic agents. Many of the presently available diuretic-saluretic agents have a tendency upon administration to induce hyperuricemia which may precipitate uric acid or sodium urate, or both, in the human body which condition may cause from mild to severe cases of gout. The compounds of Formula I provide an effective tool to treat those patients (both human and animal) requiring treatment for hyperuricemia without incurring the risk of gout.

Applicants have found that, in a more preferred embodiment of this invention, a compound of Formula I wherein R is 2-thienyl thus being [2,3-dichloro-4-(2-thenoyl)phenoxy]acetic acid exhibits particularly good hyperuricemic activity in that it can cause a sharp increase in uric acid excretion and a decrease in plasma uric acid concentration.

The pharmaceutically acceptable salts of the compounds in Formula I which are useful in treating hyperuricemia are generally any pharmaceutically acceptable non-toxic acid addition salts thereof such as the hydrochloride salt. Further, the pharmaceutically acceptable non-toxic salt can be an alkali metal salt such as the sodium salt of the acid or the addition salt of said acid with a pharmaceutically acceptable base. Of particular value as pharmaceutically acceptable bases are piperazine, N-methylpiperazine and N-methylglucamine.

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 100, 150, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 250 milligrams of a compound of Formula I or a suitable salt thereof with 172 mg. of lactose and 3 mg. of magnesium stearate and placing the 425 mg. mixture into a No. 1 gelatin capsule. Similarly, by employing more of the active ingredient and less lactose, other dosage forms can be put up in No. 1 gelatin capsules and should it be necessary to mix more than 425 mg. of the ingredients together, larger capsules may be employed. Compressed tablets, pills, or other desired unit dosages can be prepared to incorporate the compounds of this invention by conventional methods, and, if desired, can be made up as elixirs or as injectable solutions by methods well known to pharmacists. An effective amount of the drug is ordinarily supplied a dosage level of from about 2.5 mg. to about 15 mg./kg. of body weight. Preferably the range is from about 2.5 mg. to 10 mg./kg. of body weight.

The following examples are included to illustrate the preparation of a repesentative dosage form:

EXAMPLE 1

Dry-filled capsules containing 50 mg. of active ingredient per capsule

|  | Per Capsule |
| --- | --- |
| ]2,3-dichloro-4-(2-thenoyl)-phenoxy]acetic acid | 250 mg. |
| Lactose | 172 mg. |
| Magnesium Stearate | 3 mg. |
| Capsule (Size No. 1) | 425 mg. |

The [2,3-dichloro-5-(2-thenoyl)phenoxy]acetic acid is reduced to a No. 60 powder and then lactose and magnesium stearate are passed through a No.60 bolting cloth onto the powder and the combined ingredients admixed for 10 minutes and then filled into a No. 1 dry gelatin caspsule.

Similar dry-filled capsules can be prepared by replacing the active ingredient of the above example by any of the other novel compounds of this invention.

EXAMPLE 2

Parenteral Solution of N-methylpyrazinium [2,3-dichloro-5-(2-thenoyl)phenoxy]acetate 500 Mg. of N-methylpyrazinium [2,3-dichloro-5-(2-thenoyl)phenoxy]acetate are dissolved in 2 ml. of water. The solution is made up to 10 ml. with water and sterilized.

EXAMPLE 3

Dry-filled capsules containing 250 mg. of [2,3-dichloro-4-(5-methyl-2-thenoyl)phenoxy]acetic acid

|  | Per Capsule |  |
| --- | --- | --- |
| [2,3-dichloro-4-(5-methyl-2-thenoyl)phenoxy]acetic acid | 250 | mg. |
| Lactose | 172 | mg. |
| Magnesium stearate | 3 | mg. |
| Capsule (size No. 1) | 425 | mg |

The [2,3-dichloro-4-(5-methyl-2-thenoyl)phenoxy]acetic acid is reduced to a No. 60 powder and then lactose and magnesium stearate are passed through a No. 60 bolting cloth onto the powder and the combined ingredients are admixed for 10 minutes and then filled into a No. 1 dry gelatin capsule.

Similar dry-filled capsules can be prepared by replacing the phenoxyacetic acid ingredient of the above example by any of the compounds of this invention.

It will be apparent from the foregoing description that the phenoxyacetic acid compounds of Formula I and their pharmaceutically acceptable non-toxic salts thereof constitute a valuable class of compounds which are valuable uricosuric agents and useful in the treatment of conditions requiring maintenance of uric acid or decrease of uric acid levels in the body.

EXAMPLE 4

Effects of [2,3-dichloro-4-(2-thenoyl)phenoxy]acetic acid on urine flow, urate and electrolyte excretion in the chimpanzee

TABLE I

Chimpanzee M, male, 59.4 kg.

| Elapsed Minutes | Urine Flow ml/min | GFR ml/min | Plasma Urate mg/100 ml | Urate Excreted mg/min | $C_{urate}$/GFR | $Na^+$ Excreted μEq/min | $K^+$ Excreted μEq/min | $Cl^-$ Excreted μEq/min |
| --- | --- | --- | --- | --- | --- | --- | --- | --- |
| 0-20 | 1.2 | 85 | 3.70 | 0.350 | 0.111 | 84 | 60 | 46 |
| 20-40 | 0.8 | 82 | 3.62 | 0.348 | 0.117 | 66 | 65 | 42 |
| 48 | | [2,3-dichloro-4-(2-thenoyl)phenoxy]acetic acid, 5 mg/kg orally | | | | | | |
| 60-80 | 2.4 | 88 | 3.62 | 1.18 | 0.369 | 331 | 99 | 361 |
| 80-100 | 3.2 | 83 | 3.48 | 1.57 | 0.543 | 433 | 106 | 485 |
| 100-120 | 3.0 | 88 | 3.48 | 1.44 | 0.472 | 471 | 116 | 523 |
| 120-140 | 3.2 | 94 | 3.18 | 1.49 | 0.499 | 499 | 121 | 559 |
| 140-160 | 3.0 | 90 | 3.25 | 1.44 | 0.492 | 457 | 115 | 514 |
| 160-180 | 2.8 | 92 | 3.14 | 1.49 | 0.518 | 410 | 110 | 478 |
| 180-200 | 2.8 | 93 | 3.01 | 1.44 | 0.515 | 434 | 107 | 483 |
| 200-225 | 2.9 | 104 | 2.91 | 1.18 | 0.391 | 442 | 100 | 492 |

Test Methods

The renal clearance of endogenous urate relative to inulin clearance (glomerular filtration rate) was measured in mature male chimpanzees lightly restrained with phenycyclidine after an intramuscular dose of 1 mg/kg. Atropine sulfate (0.02 mg/kg s.c.) was also administered to check any excess salivation. Supplementary phencyclidine was given as needed. Priming doses of inulin (50 mg/kg.) and para-aminohippurate (8 mg/kg) to measure effective renal plasma flow were administered intravenously through a polyethylene catheter placed in one saphenous or brachial vein, followed by a constant infusion at 3 ml/min calculated to maintain plasma levels of inulin and PAH at approximately 50 and 1.5 mg/100 ml, respectively. After a 1-hour equilibration period, urine was quantitatively collected via a sterile bladder catheter inserted into the urinary bladder for 20-minute periods followed by two bladder rinses with sterile water and a final air rinse. Heparinized blood samples were collected at the midpoint of each urine collection period from a sterile polyethylene catheter placed in a contralateral saphenous or brachial vein. Control periods were secured prior to oral doses of [2,3-dichloro-4-(2-thenoyl)phenoxy]acetic acid. Experimental periods were monitored for 2 to 2½ hours. Effects on $C_{urate}/C_{inulin}$, sodium, potassium and chloride excretion are tabulated above.

Test Results

An oral of 5 mg/kg of [2,3-dichloro-4-(2-thenoyl)phenoxy]acetic acid elicited an increase in $C_{urate}/C_{inulin}$ from a control value of 0.114 to a maximum value of 0.518 representing approximately a 4.5 fold increase in the clearance ratio.

What is claimed is:

1. Method of maintaining or decreasing uric acid levels in the body which comprises administering to a patient in need thereof a uricosuric effective amount in unit dosage form of a compound of the formula:

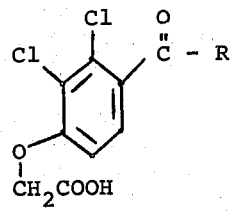

I wherein R is 2-thienyl, 5-methyl-2-thienyl or 2furyl and the alkali metal salt of a said acid and addition salts of a said acid with a pharmaceutically acceptable base.

2. The method of claim 1 wherein the mode of administration is oral or intravenous and the dosage amount is 100 mg to 500 mg of the compound.

3. The method of claim 1 wherein the compound is [2,3-dichloro-4(2 thenoyl) phenoxy]acetic acid.

4. Method of claim 1 wherein the base is selected from the group consisting of piperazine, N-methyl piperazine and N-methyl glucamine.

* * * * *

Notice of Adverse Decision in Interference

In Interference No. 99,606 involving Patent No. 3,958,004, E. J. Cragoe, Jr., and G. M. Fanelli, Jr., PHENOXYACETIC ACID DERIVATIVES AS URICOSURIC AGENTS, final judgment adverse to the patentees was rendered July 31, 1978, as to claims 1–4.

[*Official Gazette October 17, 1978.*]